United States Patent
Huang

(10) Patent No.: US 10,210,307 B2
(45) Date of Patent: Feb. 19, 2019

(54) METHOD OF DETERMINING PROTEIN EXPRESSION

(71) Applicants: RayBioTech, Inc. Guangzhou, Guangzhou, OT (CN); RayBiotech Life, Inc., USA, Norcross, GA (US)

(72) Inventor: Ruo-Pan Huang, Johns Creek, GA (US)

(73) Assignees: RayBiotech, Inc. Guangzhou, Guangzhou (CN); RayBiotech Life, Inc., USA, Norcross, GA (US)

( * ) Notice: Subject to any disclaimer, the term of this patent is extended or adjusted under 35 U.S.C. 154(b) by 0 days.

(21) Appl. No.: 15/581,440

(22) Filed: Apr. 28, 2017

(65) Prior Publication Data

US 2018/0314792 A1    Nov. 1, 2018

(51) Int. Cl.
| | |
|---|---|
| *G06F 19/20* | (2011.01) |
| *G01N 33/68* | (2006.01) |
| *G01N 33/558* | (2006.01) |
| *G01N 1/00* | (2006.01) |
| *G01N 1/14* | (2006.01) |

(52) U.S. Cl.
CPC .............. *G06F 19/20* (2013.01); *G01N 1/00* (2013.01); *G01N 33/558* (2013.01); *G01N 33/6893* (2013.01); *G01N 2001/002* (2013.01); *G01N 2001/149* (2013.01)

(58) Field of Classification Search
CPC ........ G06F 19/20; G01N 1/00; G01N 33/558; G01N 33/6893
See application file for complete search history.

(56) References Cited

U.S. PATENT DOCUMENTS

| | | | | |
|---|---|---|---|---|
| 4,935,208 A | * | 6/1990 | Kohler | .................... B01L 9/52 206/558 |
| 6,428,668 B1 | * | 8/2002 | Ansorge | ........... G01N 27/44743 204/456 |
| 2002/0188263 A1 | * | 12/2002 | Le Bui | ............. A61B 5/150022 604/358 |
| 2013/0344478 A1 | * | 12/2013 | Xia | ....................... B01L 3/5023 435/5 |

* cited by examiner

*Primary Examiner* — Melanie Yu Brown
(74) *Attorney, Agent, or Firm* — Thomas | Horstemeyer, LLP

(57) ABSTRACT

Provided are embodiments of a method for determining a serum protein biomarker profile of a subject patient comprising: wicking blood from a subject onto a fluid sample collecting comb consisting of absorbent strips, each absorbent strip consisting of a fibrous absorbent wick configured to absorb a predetermined volume of blood; drying the blood samples on the wicks and eluting serum proteins into an elution buffer; determining the identities and levels of the extracted proteins by microarray analysis; comparing by computer the identities and levels of the extracted proteins with a reference database generated from the blood samples from a plurality of subjects collected by a fluid sample collecting comb and producing a computer-generated report of the identities and levels of the biomarkers of the subject and adjusting the treatment based on the identities and amounts of the protein biomarkers of the blood sample of the subject.

13 Claims, 7 Drawing Sheets

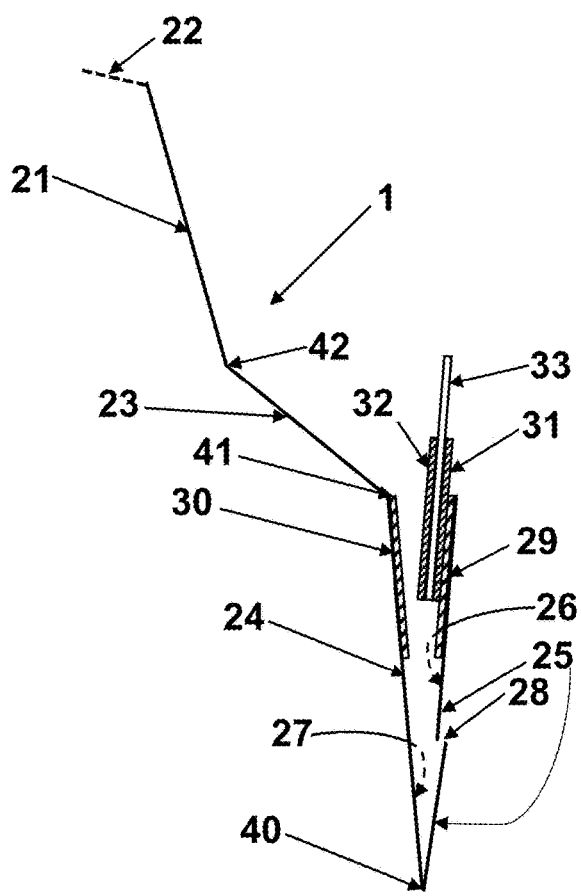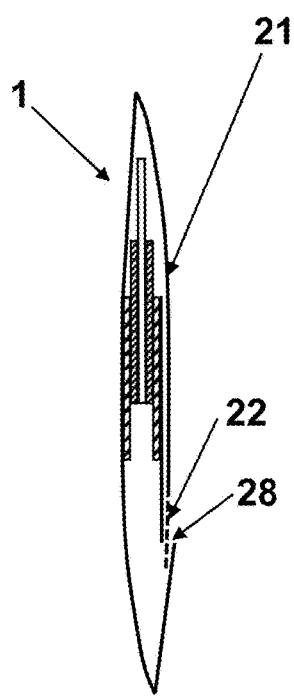
*Fig. 2A*  *Fig. 2B*

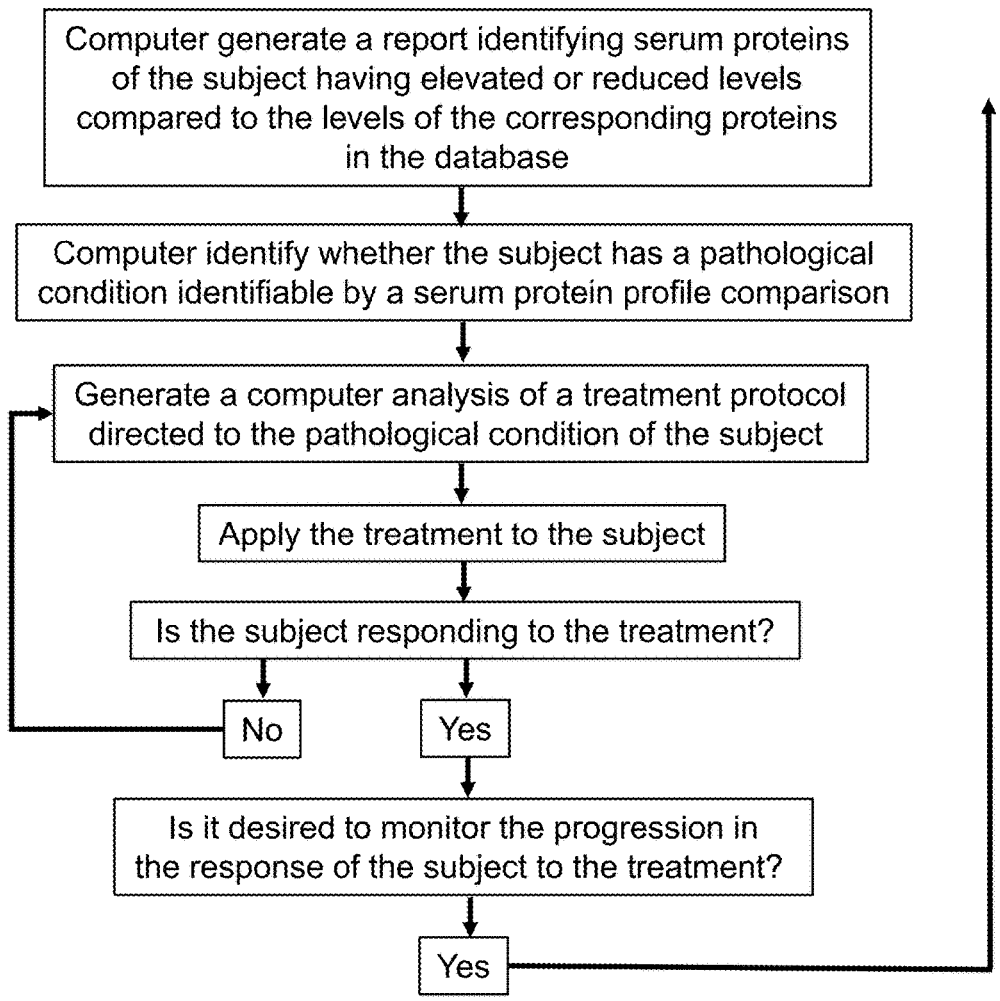
*Fig. 4-cont'd*

METHOD OF DETERMINING PROTEIN EXPRESSION

TECHNICAL FIELD

The present disclosure is generally related to a method of determining protein expression. The disclosure further relates to a biological fluid sample collection device and to methods of use thereof.

BACKGROUND

Personalized medicine often requires obtaining a genetic or protein profile of a patient, relating that profile to a pathological condition and then determining the most appropriate course of treatment, including drug selection and dosage levels. Monitoring of the treatment and adjusting the protocol in accordance with the progress of the patient may also be required.

Serum blood proteins may be indicative of a pathology and may change in response to drug administration to the patient. Most typically, blood samples are gathered by venal insertion of a needle and the collection of blood in milliliter amounts. Anticoagulants may be included to maintain the sample in the liquid state and the serum is obtained after centrifugation to remove cellular and particulate matter.

With the development of microarray analysis techniques, the use of far smaller blood serum samples than had been previously necessary for other analytical techniques is now possible. What is needed, therefore, is a means of collecting such small-volume samples in a form that can be readily stored with reduced or zero deterioration in the sample and which allows untrained persons, including the subject patient, to obtain the blood samples without the need of a trained technician to be present and subsequently transmit the sample to an analytical facility.

SUMMARY

Briefly described, one aspect of the disclosure encompasses embodiments of a method of determining the identities and the expression levels of serum protein biomarkers of a human or animal subject, the method comprising the steps of: (a) contacting blood from a subject animal or human with a fluid sample collecting comb, said comb consisting of a plurality of absorbent strips, wherein each absorbent strip consists of a fibrous absorbent wick having a proximal end disposed between and adhering to a first holding strip and a second holding strip and a distal end extending from the holding strips, and wherein the plurality of fibrous absorbent strips is disposed between a first gripping sheet and a second gripping sheet and wherein the plurality of fibrous absorbent strips are attached to the first gripping sheet and optionally the second gripping sheet; (b) allowing the blood samples absorbed by the fibrous absorbent wicks to dry; (c) eluting serum proteins from the blood samples by incubating said wicks with an elution buffer; (d) determining the identities and levels of the extracted proteins of the subject sample by microarray analysis; (e) comparing by computer the identities and levels of the extracted proteins of the subject sample with a reference database generated from the blood samples of a plurality of subjects; (f) producing a computer-generated report of the identities and levels of the serum protein biomarkers of the subject, comparing the reported levels of the serum protein biomarkers with the average levels of the same protein biomarkers of the reference database and identifying if the subject has elevated or reduced level of at least one biomarker compared to the level of the biomarker in the database; (g) producing a computer-generated report associating an elevated or reduced level of at least one biomarker of the subject with a pathological condition in need of a treatment; and (h) adjusting the treatment based on the identities and amounts of the protein biomarkers of the blood sample of the subject.

In some embodiments of this aspect of the disclosure the microarray analysis can be performed using a low density microarray, an expression microarray, a proteomic array, or an antibody array.

In some embodiments of this aspect of the disclosure the microarray analysis can comprise identifying a statistical significance level for whether a gene is upregulated or downregulated relative to a reference.

In some embodiments of this aspect of the disclosure a prioritized list of candidate treatments can be identified.

In some embodiments of this aspect of the disclosure prioritizing comprises ordering the treatments from higher priority to lower priority according to usable analysis results for serum protein products using microarray analysis.

In some embodiments of this aspect of the disclosure the method can further comprise administration of the one or more candidate treatment to the subject.

In some embodiments of this aspect of the disclosure the report can lists the one or more identified candidate treatments and the biomarker-drug association rules used to identify the one or more identified candidate treatments.

In some embodiments of this aspect of the disclosure the report comprises a summary listing of the microarray analysis.

In some embodiments of this aspect of the disclosure the report is displayed using a computer display or a printed report.

Another aspect of the disclosure encompasses embodiments of a biological fluid sample collector comprising a sample collecting comb, said comb consisting of a plurality of absorbent strips, wherein each absorbent strip consists of a fibrous absorbent wick having a proximal end disposed between and adhering to a first holding strip and a second holding strip and a distal end extending from the holding strips, and wherein the plurality of fibrous absorbent strips is disposed between a first gripping sheet and a second gripping sheet and wherein the plurality of fibrous absorbent strips are attached to the first gripping sheet and optionally the second gripping sheet.

In some embodiments of this aspect of the disclosure the biological fluid sample collector can further comprise a foldable cover extending from the first gripping sheet and wherein the distal end of the foldable cover is removably secured to the second gripping sheet, thereby enclosing the plurality of fibrous absorbent strips of the sample collecting comb.

In embodiments of this aspect of the disclosure the fibrous absorbent strips can be comprised of absorbent paper, glass fibers, a fibrous polymer, or any combination thereof.

Still another aspect of the disclosure encompasses a kit comprising packaging containing a biological fluid sample collector according to the disclosure, a means to obtain a biological fluid from a human or animal subject, and instructions for obtaining a biological fluid from a human or animal subject and collecting a sample therefrom using the biological fluid sample collector.

In some embodiments of this aspect of the disclosure the means to obtain a biological fluid is a lancet.

Yet another aspect of the disclosure encompasses embodiments of a method of obtaining a biological fluid sample from a subject animal or human comprising the steps of: (a) contacting a biological fluid from a subject animal or human with a sample collecting comb consisting of a plurality of fibrous absorbent strips, wherein each fibrous absorbent strip has a proximal end disposed between and adhering to a first holding strip and a second holding strip and a distal end extending from the holding strips, and wherein the plurality of fibrous absorbent strips is disposed between a first gripping sheet and a second gripping sheet and wherein the plurality of fibrous absorbent strips are attached to the first gripping sheet and optionally the second gripping sheet; and (b) incubating the plurality of fibrous absorbent strips having the biological fluid sample absorbed thereon with an elution buffer, thereby eluting the biological fluid sample from the fibrous absorbent strips.

In some embodiments of this aspect of the disclosure the method can further comprise the step of drying the biological fluid samples absorbed on the five fibrous absorbent strips.

In some embodiments of this aspect of the disclosure the elution buffer can comprise phosphate buffer saline, a protease inhibitor, and a detergent.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 2A illustrates a vertical section of an embodiment of a biological fluid sample collector according to the disclosure and having a foldable cover in an open extended configuration.

FIG. 2B illustrates a vertical section of an embodiment of a biological fluid sample collector according to the disclosure and having a foldable cover in a closed configuration to form a cover over a sample collecting comb.

DETAILED DESCRIPTION

Figure 1:
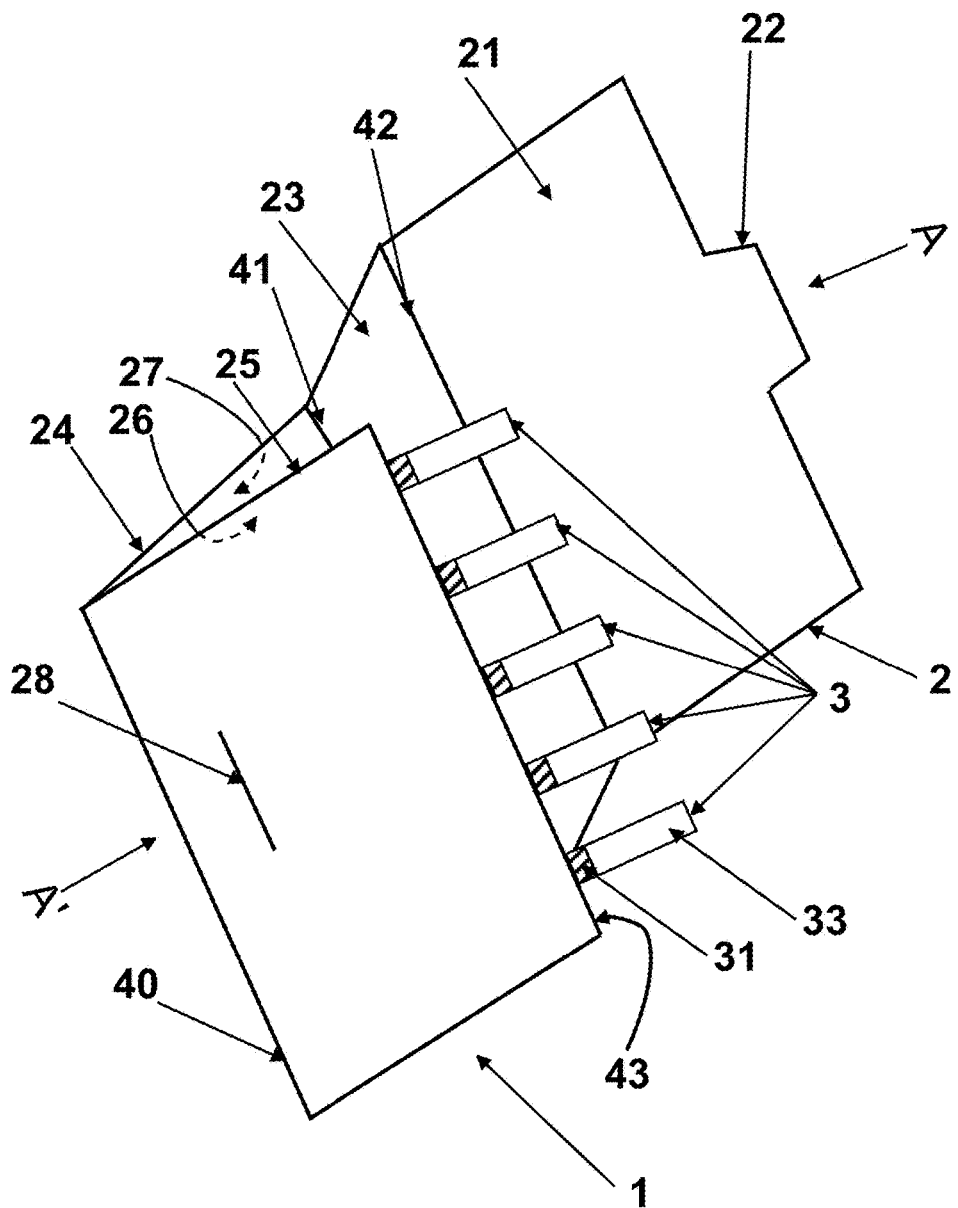
FIG. 1 is a perspective view of an embodiment of a biological fluid sample collector according to the disclosure and having a sample collecting comb consisting of five fibrous absorbent strips. A-A' indicates a vertical plane through the collector.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to embodiments encompassed by the present disclosure refers to devices or methods like those disclosed herein, but which may contain additional structural features or method steps. Such additional structural features or method steps, etc., however, do not materially affect the basic and novel characteristic(s) of the devices or methods, compared to those of the corresponding devices or methods disclosed herein.

Definitions

The term "detecting molecule array" as defined herein refers to a plurality of detection molecules that may be protein-based detecting molecules (specifically, antibodies, fragments of antibodies, or any combinations thereof), optionally attached to a support where each of the detecting molecules is attached to a support in a unique pre-selected and defined region.

The different detecting molecules for each target may be spatially arranged in a predetermined and separated location in an array. An array may be any solid support holding in distinct regions (dots, lines, columns) different and known, predetermined detecting molecules.

As used herein, "substrate" or "support" or "solid support", when referring to an array, refers to a material having a rigid or semi-rigid surface. Often, the substrate is a silicon or glass surface, (poly)tetrafluoroethylene, (poly) vinyldiene difluoride, polystyrene, polycarbonate, a charged membrane, such as nylon or nitrocellulose, or combinations thereof. Preferably, at least one surface of the substrate may be substantially flat. The support may optionally contain reactive groups, including, but not limited to, carboxyl, amino, hydroxyl, thiol, and the like. In one embodiment, the support may be optically transparent.

It should be further appreciated that any of the reagents, substances or ingredients included in any of the methods of the disclosure may be provided as reagents embedded, linked, connected, attached, placed or fused to any of the solid support materials described above.

The terms "level of expression" or "expression level" are used interchangeably and generally refer to a numerical representation of the amount (quantity) of protein biomarker in a biological sample. "Expression" generally refers to the process by which gene-encoded information is converted into the structures present a biological subject. Fragments of the translated protein, or the post-translationally modified protein shall also be regarded as expressed whether they originate from a transcript generated by alternative splicing or a degraded transcript, or from a post-translational processing of the protein, e.g., by proteolysis. Methods for determining the level of expression of the biomarkers of the disclosure will be described in more detail below.

The term "expression value" refers to the result of a calculation that uses as an input the "level of expression" or "expression level" obtained experimentally and by normalizing the "level of expression" or "expression level" by at least one normalization step as detailed herein, the calculated value termed herein "expression value" is obtained.

More specifically, as used herein, "normalized values" are the quotient of raw levels of serum biomarkers divided by the expression value of a control reference gene from the same sample, such as a stably-expressed housekeeping control gene. Any assayed sample may contain more or less biological material than is intended, due to human error and equipment failures. Importantly, the same error or deviation applies to both the biomarkers of the disclosure and to the control reference biomarker.

Normalized level values of the biomarkers of the disclosure that are higher (positive) or lower (negative) in comparison with a corresponding predetermined standard expression value or a cut-off value in a control sample predict to which population of patients the tested sample belongs. It should be appreciated that an important step in the prognostic method of the disclosures is determining whether the normalized expression value of any one of the biomarkers of the disclosure is changed compared to a pre-determined cut off.

The term "comparing" as used herein denotes any examination of the expression level and/or expression values obtained in the samples of the disclosure as detailed throughout in order to discover similarities or differences between at least two different samples. It should be noted that comparing according to the present disclosure encompasses the possibility to use a computer-based approach. In embodiments, the method of the disclosure can involve calculating and determining if the expression value obtained is any one of, positive, negative or equal to a predetermined standard expression value, or cutoff value. Such a step involves calculating and measuring the difference between the expression values of the examined sample and the cutoff value and determining whether the examined sample can be defined as positive or negative.

The term "cutoff value", sometimes referred to simply as "cutoff" as used herein refers to a value that meets the requirements for both high diagnostic sensitivity (true positive rate) and high diagnostic specificity (true negative rate).

The terms "sensitivity" and "specificity" as used herein refer to the ability of one or more markers to correctly classify a sample as belonging to a pre-established population associated with responsiveness or alternatively, non-responsiveness to treatment or to a specific relapse rate.

"Sensitivity" indicates the performance of the biomarkers of the disclosure with respect to correctly classifying samples as belonging to pre-established populations that are likely to respond to a therapy. "Sensitivity" relates to the rate of correct identification of responsiveness in samples as such out of a group of samples, whereas "specificity" relates to the rate of correct identification of lack of responsiveness in samples as such out of a group of samples. Cutoff values may be used as a control sample, said cutoff values being the result of a statistical analysis of the serum biomarker expression values differences in pre-established populations healthy, responsive or nonresponsive.

"Specificity" indicates the performance of the biomarkers of the disclosure with respect to correctly classifying samples as belonging to pre-established populations that are likely to not respond to treatment.

Thus, a given population having specific clinical parameters will have a defined likelihood to respond to a treatment based on the expression values of the biomarkers being above or below said cutoff values. It should be emphasized that the nature of the disclosure is such that the accumulation of further patient data may improve the accuracy of the cutoff values.

The term "predicting responsiveness" as used herein refers to determining the likelihood that the subject will respond to treatment, namely the success or failure of treatment.

The term "response" or "responsiveness" to treatment refers to an improvement in at least one relevant clinical parameter as compared to an untreated subject diagnosed with the same pathology (e.g., the same type, stage, degree and/or classification of the pathology), or as compared to the clinical parameters of the same subject prior to treatment.

The term "specific probability" as used herein refers to a probability of a patient to respond to treatment, wherein the probability is calculated according to the patient population analysis provided herein, but may be further fine-tuned as more patient clinical data is accumulated and the same statistical analysis may be reiterated using the augmented clinical population database.

The phrase "assessing the responsiveness or evaluating efficacy of treatment" As used herein refers to determining the likelihood (predicting) that treatment is efficient or non-efficient in treating a specific condition, e.g., the success or failure of the treatment in treating the condition in a subject in need thereof.

The term "efficacy" as used herein refers to the extent to which treatment produces a beneficial result, e.g., an improvement in one or more symptoms of the pathology (caused by the condition to be treated) and/or clinical parameters related to the pathology as described herein below. For example, the efficacy of treatment may be evaluated using standard therapeutic indices for each condition separately being for example, an infectious disease (or alternatively, an autoimmune disease or a proliferative disorder).

The efficacy of treatment can be a long-term efficacy. The phrase "long-term efficacy" as used herein refers to the ability of a treatment to maintain a beneficial result over a period of time, e.g., at least about 16 weeks, at least about 26 weeks, at least about 32 weeks, at least about 36 weeks, at least about 40 weeks, at least about 48 weeks, at least about 52 weeks, at least about 18 months, at least about 24 months, at least about 3 years, at least about 4 years, at least about 5 years, at least about 6 years, at least about 7 years, at least about 8 years, at least about 9 years, at least about 10 years, or longer.

The term "relapse", as used herein relates to the re-occurrence of a condition, disease or disorder that affected a person in the past. Specifically, the term relates to the re-occurrence of a disease being treated with interferon.

As used herein the phrase "treatment" refers to administration of into a subject in need thereof. It should be noted that administration of may comprise a single or multiple dosages, as well as a continuous administration, depending on the pathology to be treated and a clinical assessment of the subject receiving the treatment.

The term "antibody" as used in this disclosure includes whole antibody molecules as well as functional fragments thereof, such as Fab, F(ab')2, and Fv that are capable of binding with antigenic portions of the target polypeptide. The antibody is preferably monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition", which as used herein refers to a preparation of antibodies or fragments thereof of single molecular composition. The antibody can be a human antibody, a chimeric antibody, a recombinant antibody, a humanized antibody, a monoclonal antibody, or a polyclonal antibody. The antibody can be an intact immunoglobulin, e.g., an IgA, IgG, IgE, IgD, 1 gM or subtypes thereof. The antibody can be conjugated to a functional moiety (e.g., a compound which has a biological or chemical function. The antibody used by the disclosure interacts with a polypeptide that is a product of biomarkers with high affinity and specificity. The term "antibody" also encompasses antigen-binding fragments of an antibody, for example, Fab, Fab', (Fab')2, Fv, Single chain antibody ("SCA", or ScFv), or any combination thereof.

Methods of generating such antibody fragments are well known in the art (See for example, Harlow and Lane, Antibodies: A Laboratory Manual, Cold Spring Harbor Laboratory, New York, 1988, incorporated herein by reference).

Purification of serum immunoglobulin antibodies (polyclonal antisera) or reactive portions thereof can be accomplished by a variety of methods known to those of skill in the art including precipitation by ammonium sulfate or sodium sulfate followed by dialysis against saline, ion exchange chromatography, affinity or immuno-affinity chromatography as well as gel filtration, zone electrophoresis, etc.

Still further, for diagnostic and monitoring uses described herein after, the antibodies used by the present disclosure may optionally be covalently or non-covalently linked to a detectable label. The term "labeled" can refer to direct labeling of the antibody via, e.g., coupling (i.e., physically linking) a detectable substance to the antibody, and can also refer to indirect labeling of the antibody by reactivity with another reagent that is directly labeled. Useful labels in the present disclosure include magnetic beads (e.g. DYNABEADS), fluorescent dyes (e.g., fluorescein isothiocyanate, Texas red, rhodamine, green fluorescent protein, and the like).

The term "selectively bind" as used herein in the context of proteins encompassed by the disclosure refers to the specific interaction of any two of a peptide, a protein, a polypeptide an antibody, wherein the interaction preferentially occurs as between any two of a peptide, protein, polypeptide and antibody preferentially as compared with any other peptide, protein, polypeptide and antibody.

The terms "disease", "disorder", "condition" and the like as used herein as they relate to a subject's health are used interchangeably and have meanings ascribed to each and all of such terms.

The terms "patient" or "subject in need" as used herein refer to any organism that may be affected by the above-mentioned conditions, and to whom the treatment and diagnosis methods herein described is desired, including humans. More specifically, the composition of the disclosure is intended for mammals. By "mammalian subject" is meant any mammal for which the proposed therapy is desired, including human, equine, canine, and feline subjects, most specifically humans.

The term "method" as used herein refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "about" as used herein indicates values that may deviate up to 1 percent, more specifically 5 percent, more specifically 10 percent, more specifically 15 percent, and in some cases up to 20 percent higher or lower than the value referred to, the deviation range including integer values, and, if applicable, non-integer values as well, constituting a continuous range. It must be noted that, as used in this specification and the appended claims, the singular forms "a", "an" and "the" include plural referents unless the content clearly dictates otherwise.

Description

The present disclosure encompasses embodiments of a method to both identify and quantify the protein biomarkers in the serum of a subject. Blood samples can be obtained from the subject most advantageously by contacting a volume of freshly exuded blood from the patient with a biological fluid sample collector as herein described. This collector has the advantages that it is simple to operate, requiring only that the absorbent wicks be contacted with the liquid blood to allow wicking of the blood. Other than the action of piercing the skin of the subject patient, which may be readily performed even by the patient and using a sterile piercing device such as a lancet well-known in the art, no further action is required. The wicked blood may be air-dried for storage or transportation to a facility that can then perform the necessary analytical procedures. It has been found that such dried blood can usefully provide serum biomarkers even when stored at room temperature for up to about two months, but can further preserve the biomarkers for much longer periods by temperatures below 0° C. and almost indefinitely at −80° C. or less.

Advantages of the use of the biological fluid sample collector of the disclosure for collecting blood samples further include it not being necessary to obtain milliliter volumes of blood, a process that would require a trained technician rather than the patient alone, and the use of anti-clotting agents. Most advantageously, and as described below, the wicks of the collector can be configured such that removal of a defined region of the wick provides a predetermined and desired amount of the dried blood suitable for the analytical procedure to be applied. For example, but not intended to be limiting, the sample volumes can be 20 µl per wick and five such wicks can provide sufficient serum for a microarray analysis as herein described.

Most conveniently, the biological fluid sample collector can be provided to the patient or a third-party as a component of a kit that can include, but is not limited to, a lancet for piercing skin, a means of transmitting the collector with the sample to a processing facility, and instructions for their use.

The serum biomarker proteins in the collected sample cab be identified and quantified by first eluting the proteins from the wicks using a selected buffer that protects the integrity of the biomarker complement from degradation, allows for their elution from the absorbent wicks, while also preserving their relative amounts.

The serum biomarkers eluted from the collector wicks may be most advantageously assayed by application to microarrays selected for the detection of a panel of biomarkers including cytokines, and other desired biomarkers of diagnostic significance and which are known in the art. The presence and quantity of the biomarkers in the applied sample are determined by detecting signals generated using methods known in the art or determined as appropriate for use with the microarrays selected.

The detected signals may be compared both qualitatively and quantitatively with a database previously generated by obtaining and analyzing samples from a plurality of subjects. Most desirably, the subjects of the database have been selected to eliminate those subjects having a pathological condition that it is desired to detect in the subject providing the test blood sample or samples. It is further desirable that the data comprising the database is obtained from blood samples using the biological fluid sample collector of the disclosure and eluted by the same procedures including elution buffer to avoid the possibility that, for example, the serum biomarker profile is modified when compared to blood collected and maintained in liquid form with the addition of anticoagulants.

The microassay data generated from a subject blood sample and the comparison with the database may then be subjected to a computer-based analysis to generate a printed report that identities the biomarkers present in the serum sample, their amounts relative to each other and/or normalized to a control marker protein, and identifies and quantifies those biomarkers over or under-expressed relative to the levels of the same biomarker(s) of the database and which indicate a possible pathological condition desired to be treated. The computing device can further generate a determination of a treatment protocol, including applicable drugs, dosing regimens, and the like that are tailored to the specific biomarker profile, diagnosis, prognosis, and response of the patient in need.

Figure 4:
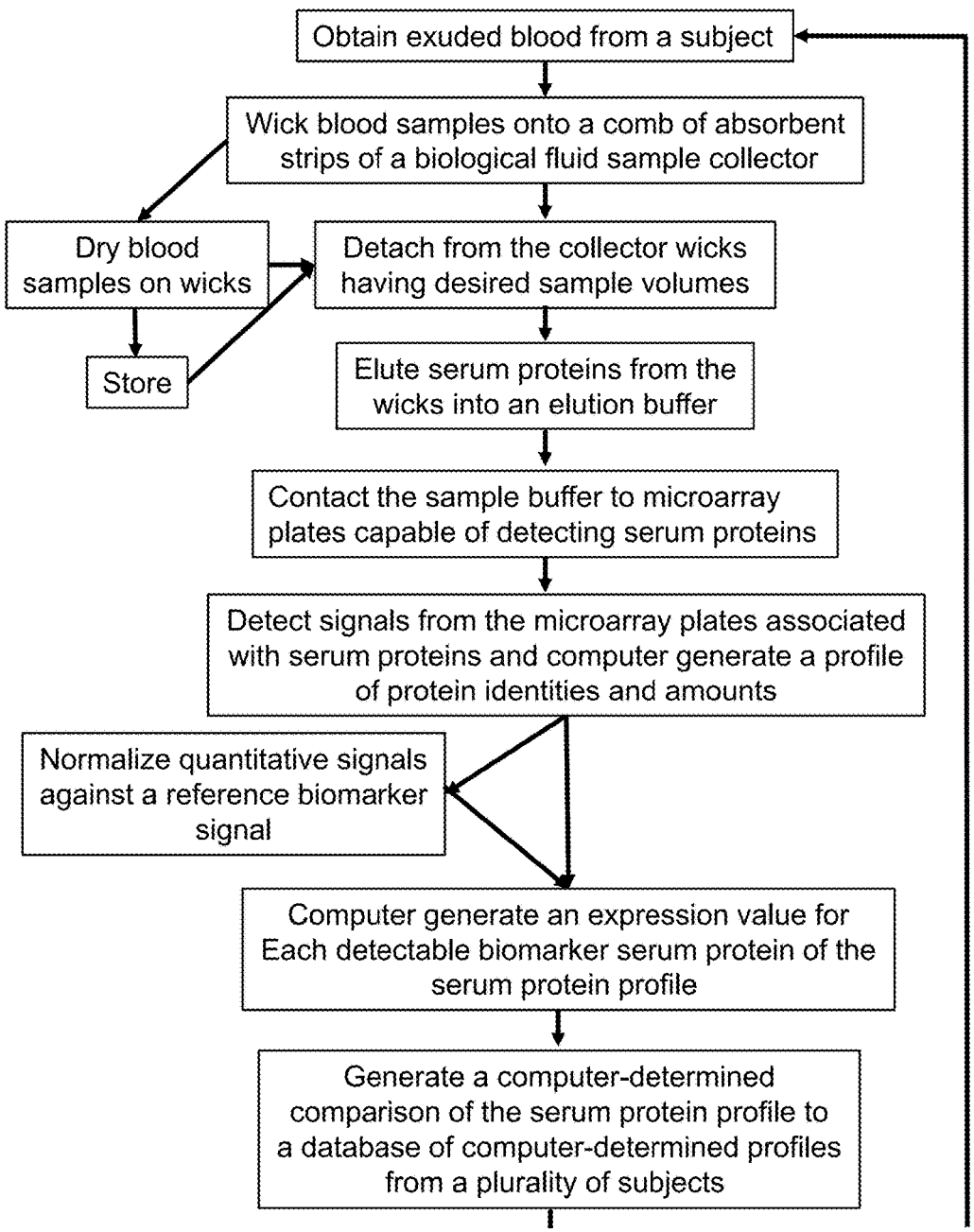
FIG. 4 illustrates a flow diagram of a method of obtaining a serum sample from a patient and determining the biomarker content of the serum.
Figure 5:
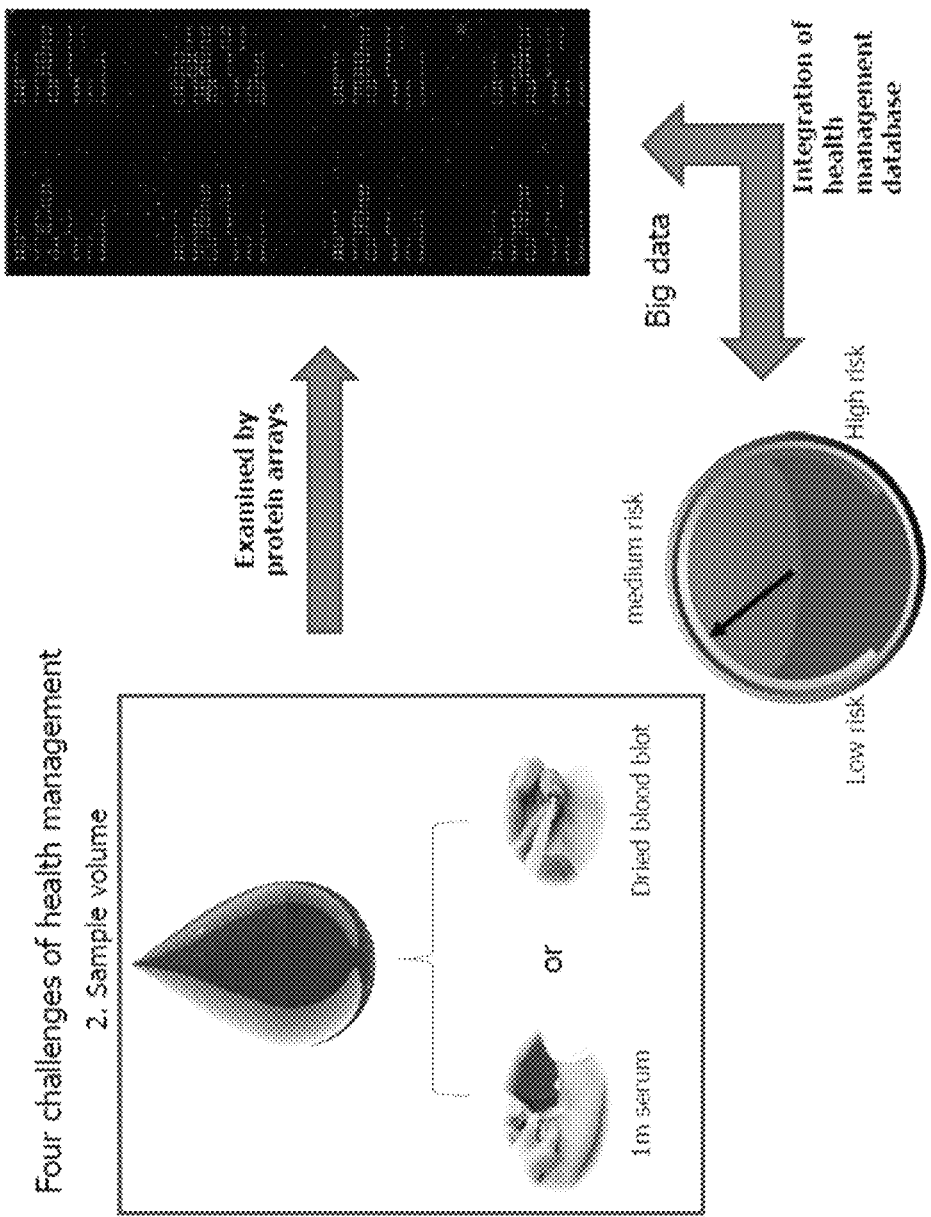
FIG. 5 illustrates a generalized scheme for the generation of a serum protein profile according to the disclosure.
Figure 6:
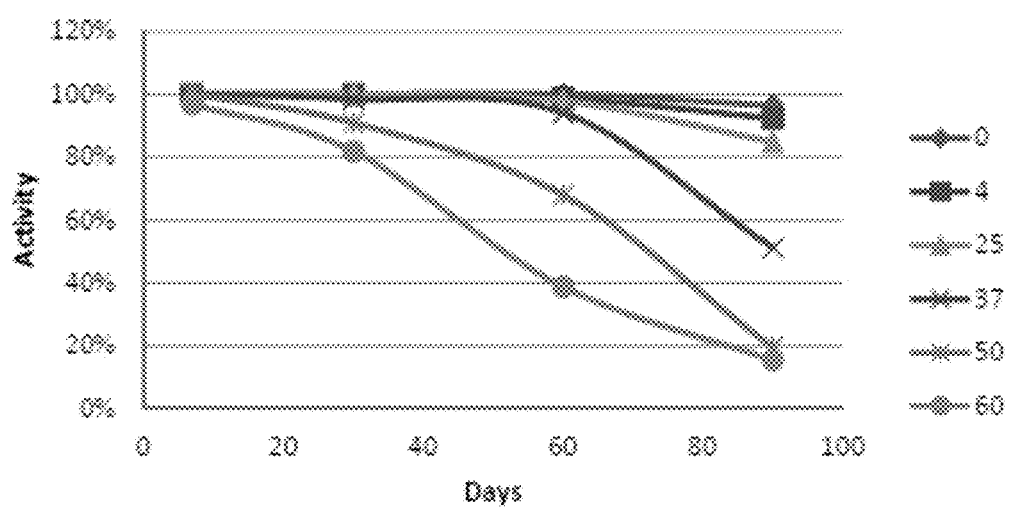
FIG. 6 is a graph illustrating the stability of dried blood serum (DBS) proteins stored at different temperatures.

The methods of the present disclosure encompass embodiments comprising at least two steps, such as shown in the flow chart of FIG. 4. First, step (a) involves determining the level of expression of serum biomarkers of a human or animal subject to obtain an expression value, or a sum of the expression values of the biomarkers. The second step (b) involves determining if the expression value obtained in step (a), or the sum of these values, is positive or negative with respect to a predetermined standard expression value, or cutoff value as recorded in a database obtained from a plurality of subjects.

It should be noted that in certain embodiments, the identities and levels of the serum biomarkers may be determined prior to a treatment, during treatment or after treatment. In specific embodiments, the method of the disclosure provides a "static" analysis, where only one sample obtained at only one time-point, preferably, prior to treatment (or alternatively, after a long period has been passed from the last treatment), is being examined.

In other embodiments, the methods of the disclosure can provide a "dynamic" analysis, where more than one sample is obtained in more than one time-point, preferably, at least one sample prior to treatment (or alternatively, after a long period has been passed from the last treatment), is being examined and at least one other sample obtained after the treatment is initiated.

In certain and specific embodiments, the method of the disclosure may further comprise an additional and optional step of normalization. According to this embodiment, in addition to determination of the level of expression of the biomarkers of the disclosure, the level of expression of at least one suitable control reference biomarker is being determined in the same sample. The next step involves comparing the normalized expression values of the serum biomarkers in the test biological sample obtained in this additional step, with a predetermined standard expression value, or a cut-off value, or with a normalized expression value of the same biomarkers in a control sample.

The second step of the method of the disclosure involves determining if the expression value obtained is positive or negative with respect to a predetermined standard expression value in at least one control sample as represented in a database acquired from subjects recognized as not having the pathological condition. Such a determination is performed by comparing the expression values determined for the tested sample with predetermined standard values or cutoff values, or alternatively, with expression values of said biomarkers in a control sample.

The expression value determined for the examined sample (or the normalized expression value) is compared with a predetermined cutoff or a control sample. More specifically, in certain embodiments, the expression value obtained for the examined sample is compared with a predetermined standard or cutoff value. In further embodiments, the predetermined standard expression value, or cutoff value has been pre-determined and calculated for a population comprising at least one of healthy subjects, subjects suffering from a disorder, non-responder subjects, subjects in remission and subjects in relapse and send data compiled in the database.

Thus, in certain embodiments, a positive expression value, or in other words, a higher expression value of the serum biomarkers as compared to the predetermined standard expression value (cutoff value), indicates that said subject belongs to a pre-established population associated with lack of responsiveness to treatment and therefore, the subject may be considered as a non-responsive subject.

Alternatively, where the expression value of the examined subject is compared with the expression value of a control sample, for example, a population of subjects that respond to treatment, a positive or higher expression value of the sample, indicates that the examined subject is a non-responsive subject. When the control sample is a population of non-responder subjects, a positive or equal expression value, indicates that the examined subject belongs to a population of subjects that lack responsiveness.

In further embodiments, where the expression value of the biomarkers of the disclosure or of a sum thereof is "negative" or lower than a control sample or a standard value of non-responder subject/s, it is indicated that the examined subject belongs to responsive population. Still further, in cases the expression value of the biomarkers or of a sum thereof is equal or lower with respect to the expression value of a control responsive subject or to the standard expression value of responders, the examined subject should be classified as belonging to responsive population.

It should be noted that according to this specific embodiment, for predicting responsiveness, determination of an expression value is performed prior to initiation of treatment. It should be appreciated that in certain embodiments, samples may be also obtained from patients that were treated long time ago (specifically, months or years before the sample is taken).

As detailed above, the prediction obtained by the method of the disclosure made by comparing between the sample and the patient population may be dependent on the selection of the population of patients to which the sample is compared to. A positive, or higher, expression value of the sample over a population of responders indicates that the examined subject is non-responsive to a mode of treatment In accordance with some embodiments, a positive expression value (or higher expression) of the biomarkers reflects a high expression of genes and is therefore indicative of a specific probability of lack of responsiveness to treatment, said probability being higher than the specific probability of responsiveness in patients where the corresponding initial expression value of the biomarkers are negative.

It should be appreciated that the cut off value is highly dependent on the size of the tested averaged group as well as the extent of homogeneity and/or heterogeneity of the tested patients. Thus, determination of the cut off value is considered a dynamic computational process that is being iteratively verified and corrected.

The disclosure further provides a method for assessing responsiveness of a mammalian subject to treatment or evaluating the efficacy of treatment on a subject. This method is based on determining the expression value of the biomarkers of the disclosure before and after initiation of treatment, and calculating the ratio of the expression as a result of the treatment. The method therefore comprises the step of:

First, in step (a), determining the level of expression of biomarkers in a biological fluid sample of the examined subject to obtain an expression value. It should be noted that the sample is obtained prior to initiation of said treatment. The second step (b) involves determining the level of expression of said biomarkers in at least one other biological fluid sample of said subject, to obtain an expression value in said sample. This at least one other sample is obtained after initiation of said treatment. In the next step (c), calculating the rate of change between the expression value obtained in step (a) before initiation, and the expression value obtained in step (b), after the initiation of the treatment. It should be noted that for determining the rate of change, the ratio between the expression value of a sample obtained after initiation of the treatment, and the expression value of a sample obtained before initiating treatment, is calculated. In certain embodiments, the ratio may be calculated between the expression values of a sample obtained before to the expression value of a sample obtained after initiation of treatment. In the next step (d), the rate of change obtained in step (c) is compared with a predetermined standard rate of change determined between at least one sample obtained prior to and at least one sample obtained following treatment. As an alternative to the use of a predetermined cutoff value of such rate of change, the method of the disclosure may involve the use of at least one control sample, and the rate of change calculated for the examined subject will be compared to the rate of change calculated for expression values in at least one control sample obtained prior and following treatment.

In some embodiments of the method of the disclosure, the fourth step (d) of the method of the disclosure involves calculating and determining if the rate of change obtained in step (c) is any one of, positive, negative or equal to a predetermined standard rate of change.

It should be noted that a positive rate of change in the expression values of biomarkers in a serum sample as compared to a predetermined standard rate of change (predetermined cutoff of the rate of change), or to the rate of change calculated for expression values in at least one control sample obtained prior and following treatment, indicates that the examined subject belongs to a pre-established population associated with responsiveness to treatment. Such result is therefore indicative of a successful therapy. This method thereby provides assessing responsiveness of a mammalian subject to treatment or evaluating the efficacy of treatment on a subject.

The method of the disclosure further provides a tool for selecting an treatment regimen for treating a subject diagnosed with a condition, by assessing and evaluating the efficacy of treatment given to a subject suffering from condition to be treated, and selecting an treatment regimen based on the evaluation; thereby selecting the treatment regimen for treating the subject diagnosed with a condition.

A treatment that either directly or indirectly affects the condition to be treated, is considered efficient in treating a condition if it exerts an improvement in at least one relevant clinical parameter related to said condition in the treated subject as compared to an untreated subject diagnosed with the same condition (e.g., where the condition is an infectious disease, such parameter may include reduction of virus load), or as compared to the clinical parameters related to the said condition of the same subject prior to the treatment.

By obtaining at least two and preferably more biological fluid samples from a subject and analyzing them according to the method of the disclosure, the prognostic method may be effective for assessing responsiveness to treatment by monitoring molecular alterations indicating a success or failure of treatment in said patient. Thus, the prognostic method of the disclosure may be applicable for early assessment. Prior as used herein is meant the first time point is at any time before initiation of treatment, ideally several minutes before initiation of treatment. However, it should be noted that any time point before initiation of the treatment, including h, days, weeks, months or years, may be useful for this method and is therefore encompassed by the disclosure. The second time point is collected from the same patient after h, days, weeks, months or even years after initiation of treatment.

In practice, for assessing response to treatment, at least two test samples (before and after treatment) should be collected from the treated patient, and preferably more. The expression levels of the serum biomarkers are then determined using the method of the disclosure, applied for each sample. As detailed above, the expression value can be obtained from the experimental expression level. The rate of change of each biomarker expression, namely, serum biomarkers or a sum thereof, is then calculated and determined by dividing the two expression values obtained from the same patient in different time-points or time intervals one by the other.

It should be noted that it is possible to divide the prior-treatment expression value by the after treatment expression value and vice versa. For the sake of clarity, as used herein, the rate of change is referred as the ratio obtained when dividing the expression value obtained at the later time point of the time interval by the expression value obtained at the earlier time point (for example before initiation of treatment).

For example, this interval may be at least one day, at least three days, at least three days, at least one week, at least two weeks, at least three weeks, at least one month, at least two months, at least three months, at least four months, at least five months, at least one year, or even more. The second point is obtained at the earlier time point that can provide valuable information regarding assessing response of the patient to treatment.

As detailed above, this rate of change calculated for the examined sample is compared with a predetermined standard rate of change. The predetermined standard rate of change may be determined between at least one sample obtained prior to and at least one sample obtained following treatment. As an alternative to the use of a predetermined cutoff value of such rate of change, the method of the disclosure may involve the use of at least one control sample, and the rate of change calculated for the examined subject may be compared to the rate of change calculated for expression values in at least one control sample obtained prior and following treatment.

The method of the disclosure can further involve calculating and determining if the rate of change obtained in step (c) is any one of, positive, negative or equal to a predetermined standard rate of change.

In accordance with some embodiments, a positive rate of change of serum biomarker expression values as compared to the predetermined standard rate of change is indicative of a specific probability to respond to treatment, said probability being higher than the specific probability of responsiveness in patients where the corresponding rate of change of serum biomarker expression values is negative.

Similarly, a negative or equal rate of change in the expression value of said biomarkers as compared to a predetermined standard rate of change is indicative of a specific probability of non-responsiveness to treatment, said probability being higher than the specific probability of non-responsiveness in patients where the corresponding rate of change of said serum biomarkers is positive.

As appreciated, the predetermined rate of change calculated for a pre-established population as detailed above for example encompasses a range for the rate of change having a low value and a high value, as obtained from a population of individuals including healthy controls, responders and non-responders. Thus, a subgroup of responsive patients can be obtained from the entire tested population. In this pre-established responsive population, the low value may be characterized by a low response whereas the high value may be associated with a high response as indicated by regular clinical evaluation. Therefore, in addition to assessing responsiveness to treatment, the rate of change may provide insight into the degree or extent of responsiveness. For example, a calculated rate of change that is closer in its value to the low value may be indicative of a low response and thus although the patient is considered responsive, increasing dosing or frequency of administration may be considered. Alternatively, a calculated rate of change that is closer in its value to the high value may be indicative of a high response, even at times leading to remission and thus lowering the administration dosage may be considered.

When referring to a pre-established population associated with responsiveness, it is meant that a statistically-meaningful group of patients treated can be analyzed as disclosed herein, and the correlations between serum biomarker expression values (and optionally other patient clinical parameters) and responsiveness to treatment was calculated. Responsiveness is associated with a population characterized by initial low expression levels of said serum biomarkers that are elevated in response to treatment, said population is a pre-established population, that is, a defined population whose responsiveness is known. Moreover, the populations may be defined by the expression (or a sum the expression values) of the serum biomarkers vis a vis the cutoff values determined by the disclosure. The population may optionally be further divided into sub-populations according to other patient parameters, for example gender and age.

The method of the disclosure may be used for personalized medicine, namely adjusting and customizing healthcare with decisions and practices being suitable to the individual patient by use of genetic information and any additional information collected at different stages of the disease.

In yet another alternative embodiment, for assessing responsiveness of a mammalian subject to treatment or evaluating the efficacy of treatment on a subject suffering from a pathologic condition, the method of the disclosure may comprise:

(a) determining the level of expression of the biomarkers of the disclosure in a biological fluid sample of said subject to obtain an expression value, wherein said sample is obtained prior to initiation of said treatment; (b) determining the level of expression of said biomarkers in at least one other biological fluid sample of said subject, to obtain an expression value, wherein said at least one other sample is obtained after initiation of said treatment; (c) comparing the expression value obtained in step (a), with the expression value obtained in step (b), or in yet further alternative specific embodiments, calculating and determining if the expression value obtained in step (a) is any one of, positive, negative or equal to the expression value obtained in step (b).

Wherein a higher expression value of serum biomarkers (or of a sum thereof) in a sample obtained after initiation of said treatment according to step (b) as compared to the expression value in a sample obtained prior to initiation of said treatment according to step (a), indicates that said subject belongs to a pre-established population associated with responsiveness to treatment.

In accordance with such an embodiment, a patient diagnosed with a disease in need for treatment is examined and a sample is obtained before initiation of treatment, the patient is then treated with according to common treatment protocol and at any time point after treatment an additional sample is obtained from the patient. The second sample may be obtained after at least 3 h, at least 4 h, at least 6 h, at least 10 h, at least 12 h, at least 24 h, at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 32 days, at least 33 days, at least 40 days, at least 50 days, at least 60 days, at least 70 days, at least 78 days, at least 80, at least 90 days, at least 100 days, at least 110, at least 120 days, at least 130 days, at least 140 days or at least 150 days after initiation of treatment.

The first sample may be analyzed at the time it was obtained from the patient or alternatively may be kept under appropriate conditions for example, under freezing conditions. The blood samples most advantageously collected by the biological fluid sample collector of the disclosure may be dried for storage at room temperature for a period of no more than about two months or indefinitely at −80° C. or less. The two samples are equally analyzed, optionally at the same time, for determining the expression of the biomarkers of the disclosure. The data obtained as an expression value are compared by normalization of the expression level as detailed herein.

Patient having a "positive" expression value (or sum of expression values of these genes) that is a higher expression value of said biomarkers of the disclosure in a sample obtained after initiation of said treatment as compared to the expression value in a sample obtained prior to initiation of said treatment according to step (a) belong to a pre-established population associated with responsiveness to treatment.

In yet other embodiments, the disclosure provides a method for monitoring disease progression or early prognosis for disease relapse. According to certain embodiments, said method comprises the steps of: First (a), determining the level of expression of serum biomarkers in a biological fluid sample of said subject to obtain an expression value. The next steps involve (b) repeating step (a) to obtain expression values of biomarkers for at least one more temporally-separated test sample. The rate of change of the expression values of said biomarkers are then calculated in step (c) between said temporally-separated test samples.

In the next step (d), the rate of change obtained in step (c) is compared with a predetermined standard rate of change (cutoff value) determined for expression value between samples obtained from at least one subject in remission and in relapse following treatment or to the rate of change calculated for expression values in at least one control sample obtained in remission and in relapse following treatment. It should be appreciated that in an alternative embodiment, step (d) of the method of the disclosure involves calculating and determining if the rate of change obtained in step (c) is any one of, positive, negative or equal to a predetermined standard rate of change.

According to certain embodiments, a negative rate of change in the expression values of serum biomarkers in said sample as compared to a predetermined standard rate (cutoff) of change or to the rate of change calculated for expression values in said at least one control sample, indicates that said subject belongs to a pre-established population associated with relapse, thereby indicating that the examined subject is in relapse. Thus, according to such embodiments, the method of the disclosure further provides early prognosis/diagnosis for monitoring disease relapse.

Prognosis is defined as a forecast of the future course of a disease or disorder, based on medical knowledge. This highlights the major advantage of the disclosure, namely, the ability to predict relapse rate in patients as soon as they are diagnosed, even prior to treatment, based on a specific genetic fingerprinting of a patient. This early prognosis facilitates the selection of appropriate treatment regimens that may minimize the predicted relapse, individually to each patient, as part of personalized medicine.

Therefore, it should be appreciated that the methods disclosed herein may further provide a tool for evaluating the extent of responsiveness of a specific individual to a specific treatment regimen. More specifically, an individual displaying lower level of expression may exhibit a more effective response to a certain treatment regimen, and therefore may require a reduced treatment regimen. In the same manner, a responsive individual showing higher levels of expression (although within the range of the responsive population), may exhibit a less effective response and thus may require an extended treatment regimen. As such, the kits and methods of the disclosure provide a clear identification of responsive individuals and also a tool for evaluating the extent of the predicted response in a given individual.

The detection step involves detecting a signal from the detecting molecules that correlates with the expression level of said serum biomarkers or product by a suitable means thereof in the sample from the subject. According to some embodiments, the signal detected from the sample by any one of the experimental methods detailed herein below reflects the expression level of said biomarkers or product thereof. Such signal-to-expression level data may be calculated and derived from a calibration curve.

In other embodiments of the disclosure, the detecting molecules used for determining the expression levels of the biomarkers of the disclosure, may be isolated detecting amino acid molecules. It should be noted that the disclosure further encompasses any combination of amino acids for use as detecting molecules for the kits, arrays, compositions and methods of the disclosure. As noted above, in the first step of the method of the disclosure, the sample or any nucleic acid or protein product derived therefrom is contacted with the detecting molecules of the disclosure.

The disclosure contemplates the use of amino acid based molecules such as proteins or polypeptides as detecting molecules disclosed herein and would be known by a person skilled in the art to measure the protein products of the biomarkers of the disclosure. As would be understood to a person skilled in the art, the measure of the level of expression of the protein products of the biomarkers of the disclosure, specifically, biomarkers requires a protein, which specifically and/or selectively binds to the biomarkers of the disclosure.

As indicated above, the detecting molecules of the disclosure may be amino acid-based molecules that may be referred to as protein/s or polypeptide/s. As used herein, the terms "protein" and 'polypeptide' are used interchangeably to refer to a chain of amino acids linked together by peptide bonds.

In specific embodiments, the detecting amino acid molecules are isolated antibodies, with specific binding selectively to the proteins encoded by serum biomarkers as detailed above.

In embodiments, the sample is advantageously a blood sample, and the method of the disclosure comprises determining the level of expression of serum biomarkers in said blood sample.

Embodiments of kits of the disclosure may, therefore, optionally comprise a suitable means for obtaining a fluid sample, and in particular a blood sample. More specifically, one must first obtain samples from the tested subjects. To do so, a means for obtaining such samples may be required. Such means for obtaining a sample from the mammalian subject can be any known in the art. Examples for obtaining blood samples are known in the art and could be any kind of finger or skin prick or lancet-based device that basically pierces the skin and results in a drop of blood being released from the skin. Most advantageously, the biological fluid sample collector of the disclosure may be used for obtaining a plurality of blood sample volumes of defined size.

It should be appreciated that the methods and kits of the disclosure may be usefully applied for assessing and monitoring responsiveness of a subject suffering from a pathological condition to a treatment. In such case, more than one sample can be obtained at different time points prior and after treatment, referred to herein as "temporally-separated samples". The kit can, therefore, further comprise instructions for calculating the rate of change of the expression values (preferably, normalized values) of biomarkers as identified by the methods of the disclosure. It should be noted that a positive rate of change of said expression values in a sample obtained after initiation of a treatment as compared to the biomarker expression value in a sample obtained prior to initiation of said treatment or to average value in a database generated from a population of patients not having the pathological condition, is indicative of the responsiveness of the subject to said treatment. The disclosure therefore provides a kit that is also applicable for a dynamic situation and is thus applicable for monitoring responsiveness and may be also used in monitoring the treated patients.

The present disclosure further encompasses embodiments of a biological fluid sample collector for the collection of a predetermined defined amount of a biological fluid for analysis of the constituents (protein or nucleic acid, for example) thereof. For example, but not intended to be limiting, the devices of the disclosure allows a blood sample of a predefined volume to be obtained from a human subject even when unskilled in the art without the participation by another, trained, individual. This allows the samples to be obtained without the patient having to travel to a facility that has the trained technician, or vice versa, and further allows the blood sample to be dried for storage and easy transportation or forwarding to a laboratory that can then conduct a desired analysis.

Referring now to FIG. 1, shown is one embodiment of the biological fluid sample collector 1 of the disclosure. This embodiment comprises two parallel gripping sheets 24, 25 connected by a hinge 40, wherein the gripping sheet 24 has an inner surface 27 facing the opposing inner surface 26 of the gripping sheet 25. In some embodiments of the biological fluid sample collector 1, the two parallel gripping sheets 24, 25 are a single sheet and the gripping sheets 24, 25 are defined by a fold or score line in the position of hinge 40. In some embodiments of the biological fluid sample collector 1, the two parallel gripping sheets 24, 25 are not attached to each other. In some embodiments of the biological fluid sample collector 1 the gripping sheet 25 includes a tab receiving slot 28.

Deposed between the inner surfaces 26 and 27, respectively, of the gripping sheets 24 and 25, and attached thereto by adhesive 29, 30 (as shown in FIG. 2A), is a plurality of sample collecting strips 3, each sample collecting strip 3 extending from the top edge 43 of at least the gripping sheet 25, said edge 43 being distal to the hinge 40, thereby forming a comb. In some embodiments the gripping sheets 24 and 25 are not attached to each other by the hinge 40 but instead attached to each other by an adhesive. Each sample collecting strip 3 consists of a fibrous absorbent wick 33 sandwiched between, and extending from, parallel holding strips 31, 32. While it is contemplated that the fibrous absorbent wick 33 and parallel holding strips 31, 32 may not be attached to each other, most advantageously the parallel holding strips are attached to the fibrous absorbent wick 33 by an adhesive. The surfaces of the parallel holding strips 31, 32 that are not contacting the sandwiched fibrous absorbent wick 33 are in contact with an adhesive (indicated in FIG. 2A as 29 and 30) disposed on the inner surfaces 26, 27 of the gripping sheets 24, 25. The extension of a fibrous absorbent wick 33 beyond the holding strips 31, 32 may be advantageously configured such that in contact with a liquid, the volume of the liquid, when absorbed up to, but not beyond the holding strips, is a desired volume.

Embodiments of the biological fluid sample collector 1 of the disclosure such as shown in FIG. 1 may further comprise a folded cover 2 comprising at least two foldably connected sheets 21, 23, wherein sheet 23 is connected to gripping sheet 24 by hinge 41 or fold and sheet 21 is connected to sheet 23 by the hinge or fold 42. Sheet 21 advantageously may be configured such that it can be folded over to enclose the comb of the plurality of sample collecting strips 3 to usefully provide a protective cover for any sample absorbed by the fibrous absorbent strips 32. When folded, the sheet 21 may be fixed to the gripping sheet 25 by any means known to one of skill in the art, including but not limited to, an adhesive, and adhesive tape, a clip, and the like. In one embodiment of the biological fluid sample collector 1, the sheet 21 further includes a tab 22 extending from sheet 21, wherein said tab 22 is configured that it may be inserted into the tab receiving slot 28 to removably fix the folded sheet 21 against the outer surface of the sheet 25.

Referring now to FIGS. 2A and 2B, illustrated are vertical sections of a biological fluid sample collector 1 of the disclosure through the plane A-A' shown in FIG. 1. Shown in FIG. 2A is a fibrous absorbent wick 33 layered between two parallel holding strips 31, 32, wherein the surface of the holding strip 31 not in contact with the fibrous absorbent wick 33 is adhered to the inner surface 26 of the gripping sheet 25 by an adhesive layer 29 on. Accordingly, the gripping sheet 24 can then be pressed against the holding strip 32 so that the adhesive layer 30 adheres to the surface of the holding strip 32 not in contact with the fibrous absorbent wick 33.

FIG. 2A illustrates the biological fluid sample collector 1 in an opened configuration that can allow the fibrous absorbent wick 33 to contact a liquid. FIG. 2B illustrates the biological fluid sample collector 1 in a folded configuration wherein the sheets 23, 21 are folded at the flexible hinges 41, 42 such that the comb of the sample collecting strips 3 is enclosed by the folded sheets 23, 21. In the embodiment shown in FIG. 2B, the tab 22 is inserted into the slot 28, thereby removably securing the sheet 21 in position.

Figure 3:
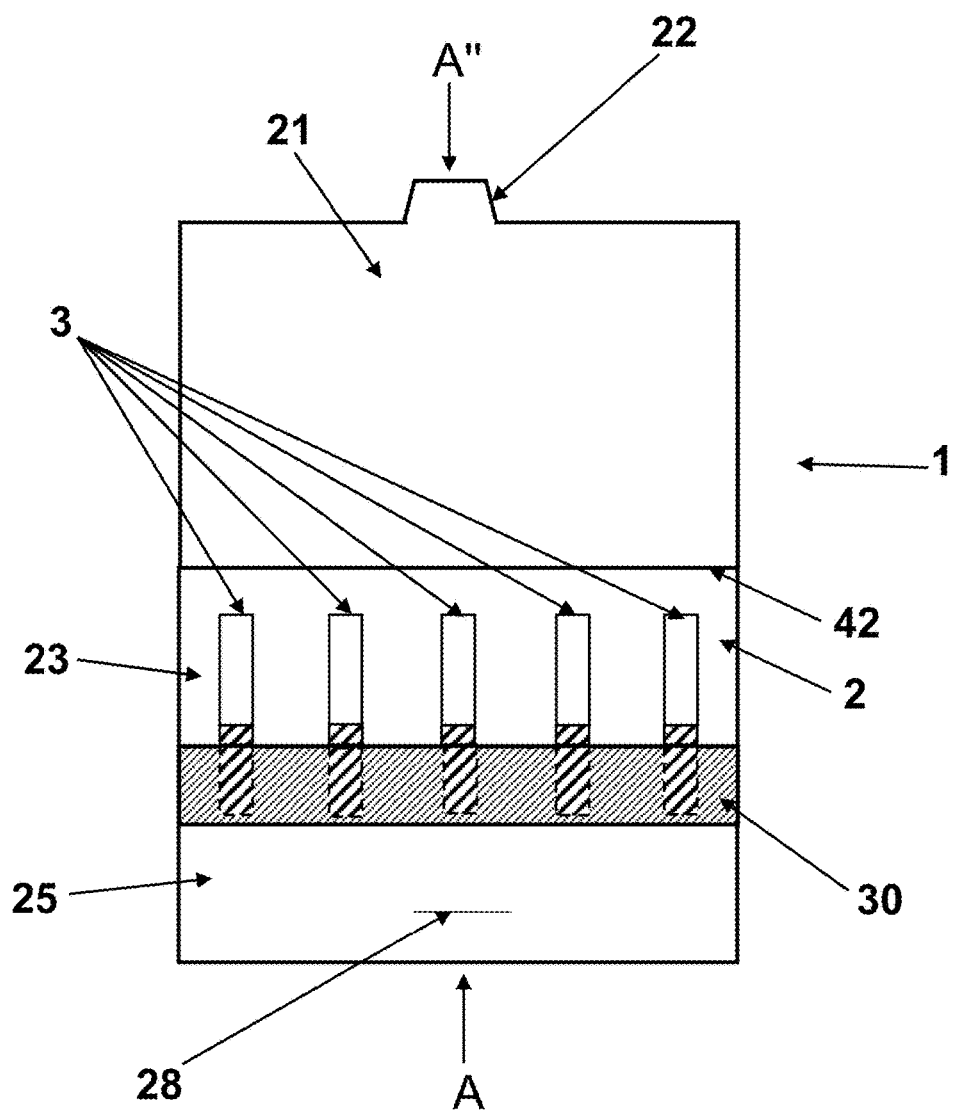
FIG. 3 illustrates a plan view of an embodiment of a biological fluid sample collector according to the disclosure and having a foldable cover in an open extended configuration.

Referring to FIG. 3, is shown a view of the device in an open configuration and further illustrating the attachment of the holding strips 31, 32 sandwiching the comb of fibrous absorbent wicks 33 to the adhesive layers 29, 30.

In the embodiments of biological fluid sample collector 1 of the disclosure, the fibrous absorbent wicks 33 may be of any absorbent material that will allow the collection of a liquid by capillary wicking including, but not limited to, absorbent (unsized) cellulose paper such as filter paper, a woven inert fibrous polymer, or a glass fiber paper. Most advantageously, the material of the fibrous absorbent wicks 33 will not interact or bind with any biological material in the collected sample in such a way as to alter the composition of the collected sample by such as degrading proteins, nucleic acids and the like or to prevent the sample's removal from the sample absorbent wick 33. Most advantageously, the material of the fibrous absorbent wicks 33 will not modulate the relative amounts of constituents as compared to the sample origin when the sample is eluted from the fibrous absorbent wicks 33.

The sheets 21, 22, 23, 24, and optionally 25, can comprise a single sheet 2, wherein the individual defined sheets 21, 22, 23, 24, and optionally 25, are defined by the hinges (or folds or score lines) 40, 41, and 42. The sheet 2 may be comprised of such as, but not limited to, paper, card, cardboard, plastic sheet and the like. Advantageously, the absorbent material may be sterilized by such as autoclaving to reduce undesirable contamination.

The biological fluid sample collector 1 of the disclosure is useful for the collection of a plurality of volumes of a liquid sample such as, but not limited to, a blood sample. For example, but not intended to be limiting, the extension of each of the fibrous absorbent strips 32 beyond the distal ends of the holding strips 31, 32 may be configured such that each fibrous absorbent wick 33 can receive 20 µl of a blood sample. By stopping the absorbing process when the liquid has reached the distal ends of the holding strips and removing the strips from the liquid source a predetermined sample volume can be readily obtained. However, it is also contemplated that the fibrous absorbent wicks 33 can be allowed to absorb a fluid beyond the distal ends of the holding strips 31, 32 but that the fibrous absorbent wicks 33 extending beyond said holding strips when removed only have absorbed the desired predetermined sample volume. The total volume of the liquid sample collected may be adjusted by the dimensions (length, width, and thickness) of the individual fibrous absorbent wicks 33 and also by the number of such strips that are used to form the comb.

The biological fluid sample collector 1 of the disclosure can be especially advantageous for the collection of a blood sample for analysis for such as genetic or protein biomarkers of a human or animal subject. For example, by collecting a blood sample with one embodiment the fluid collection device 1 having a comb of five individual fibrous absorbent wicks 33, wherein the dimensions of each the sample absorbent strips allow the collection of 20 µl, a total volume of sample can be 100 µl.

A blood sample may be obtained from a digit of a human subject by piercing the skin with a lancet or scalpel blade. Generally, lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i.e., less than 1 mL. A small amount of blood for the blood test will ooze out of the skin. There are many small blood vessels in each finger so that a finger can be squeezed to cause a larger drop of blood to ooze.

Once the blood has formed a drop judged to be of sufficient volume, for example 100 µl, the individual fibrous absorbent wicks 33 of a biological fluid sample collector 1 can be sequentially dipped into the blood drop and a sample of the blood allowed to be absorbed by wicking into each of the fibrous absorbent wicks 33. The operator can end the absorbance of the sample into each strip once the blood has reached the holding strips layered onto the strip. Once the predetermined number of strips have received the samples, the blood absorbed may be allowed to air dry, thereby reducing the possibility of degradation of the nucleic acids and proteins of the sample. When dry, the single sheet 2 can be folded at folds 41 and 42 to create a cover to protect the sample absorbent strips from any undesirable contamination and sent to a facility for extraction of the samples and their subsequent analysis. It has been found advantageous to store the device with blood samples absorbed thereto at room temperature for about two months while for prolonged storage a temperature of about −80° C. is preferred.

Samples dried onto the fibrous absorbent wicks 33 may be eluted from the device by mechanically removing the fibrous absorbent wicks 33 from the fluid collection device 1 and placing the strips individually in such as a standard microfuge tube well known to those of skill in the art. An elution buffer is then added.

The elution buffer may be formulated to preserve the integrity of the biological components desired to be analyzed and to facilitate the elution of the components from the fibrous material of the fibrous absorbent wicks 33. For example, if the protein complement of the biological fluid sample is desired, a protease inhibitor may be included in the elution buffer to prevent or reduce undesirable degradation of such as serum proteins. If nucleic acid samples are desired it is advantageous to include nuclease inhibitors. A detergent may be included assist in elution from the fibrous absorbent wicks 33 as well as preserving sample integrity.

The biological fluid sample collector 1 of the disclosure may also be included in a kit that can further comprise a means to obtain a biological fluid from a subject. For example, but not intended to be limiting, a sterile lancet may be provided that can be used to pierce the skin of a fingertip to provide at least 100 µl of blood as a drop into which the fibrous absorbent wicks 33 of the sample collecting biological fluid sample collector 1 may be dipped. The kit can further encompass packaging and instructions for use of the biological fluid sample collector 1 and the means to obtain a biological fluid.

Accordingly one aspect of the disclosure encompasses embodiments of a method of determining the identities and the expression levels of serum protein biomarkers of a human or animal subject, the method comprising the steps of: (a) contacting blood from a subject animal or human with a fluid sample collecting comb, said comb consisting of a plurality of absorbent strips, wherein each absorbent strip consists of a fibrous absorbent wick having a proximal end disposed between and adhering to a first holding strip and a second holding strip and a distal end extending from the holding strips, and wherein the plurality of fibrous absorbent strips is disposed between a first gripping sheet and a second gripping sheet and wherein the plurality of fibrous absorbent strips are attached to the first gripping sheet and optionally the second gripping sheet; (b) allowing the blood samples absorbed by the fibrous absorbent wicks to dry; (c) eluting serum proteins from the blood samples by incubating said wicks with an elution buffer; (d) determining the identities and levels of the extracted proteins of the subject sample by microarray analysis; (e) comparing by computer the identities and levels of the extracted proteins of the subject sample with a reference database generated from the blood samples of a plurality of subjects; (f) producing a computer-generated report of the identities and levels of the serum protein biomarkers of the subject, comparing the reported levels of the serum protein biomarkers with the average levels of the same protein biomarkers of the reference database and identifying if the subject has elevated or reduced level of at least one biomarker compared to the level of the biomarker in the database; (g) producing a computer-generated report associating an elevated or reduced level of at least one biomarker of the subject with a pathological condition in need of a treatment; and (h) adjusting the treatment based on the identities and amounts of the protein biomarkers of the blood sample of the subject.

In some embodiments of this aspect of the disclosure the microarray analysis can be performed using a low density microarray, an expression microarray, a proteomic array, or an antibody array.

In some embodiments of this aspect of the disclosure the microarray analysis can comprise identifying a statistical significance level for whether a gene is upregulated or downregulated relative to a reference.

In some embodiments of this aspect of the disclosure the statistical significance can be determined at a p-value of less than or equal to 0.05.

In some embodiments of this aspect of the disclosure the p-value can be corrected for multiple comparisons.

In some embodiments of this aspect of the disclosure a prioritized list of candidate treatments can be identified.

In some embodiments of this aspect of the disclosure prioritizing comprises ordering the treatments from higher priority to lower priority according to usable analysis results for serum protein products using microarray analysis.

In some embodiments of this aspect of the disclosure the method can further comprise administration of the one or more candidate treatments to the subject.

In some embodiments of this aspect of the disclosure the report can lists the one or more identified candidate treatments and the biomarker-drug association rules used to identify the one or more identified candidate treatment.

In some embodiments of this aspect of the disclosure the report comprises a summary listing of the microarray analysis.

In some embodiments of this aspect of the disclosure the report is displayed using a computer display or a printed report.

In some embodiments of this aspect of the disclosure the distal end of each fibrous absorbent wick is configured to absorb about 20 µl of a liquid.

In some embodiments of this aspect of the disclosure the biological fluid sample collector can comprise a sample collecting comb consisting of five absorbent strips, wherein each absorbent strip consists of a fibrous absorbent wick having a proximal end disposed between and adhering to a first holding strip and a second holding strip and a distal end extending from the holding strips, wherein the extending distal end of each fibrous absorbent strip is configured to absorb about 20 µl of a liquid and wherein the plurality of fibrous absorbent strips is disposed between a first gripping sheet and a second gripping sheet and wherein the plurality of fibrous absorbent strips are attached to the first gripping sheet and optionally the second gripping sheet, and further comprising a foldable cover extending from the first gripping sheet, the distal end of the foldable cover having a tab configured to be removably receivable by a slot in the second gripping sheet and wherein the distal end of the foldable cover is removably secured to the second gripping sheet, thereby enclosing the plurality of fibrous absorbent strips of the sample collecting comb.

Another aspect of the disclosure encompasses embodiments of a biological fluid sample collector comprising a sample collecting comb, said comb consisting of a plurality of absorbent strips, wherein each absorbent strip consists of a fibrous absorbent wick having a proximal end disposed between and adhering to a first holding strip and a second holding strip and a distal end extending from the holding strips, and wherein the plurality of fibrous absorbent strips is disposed between a first gripping sheet and a second gripping sheet and wherein the plurality of fibrous absorbent strips are attached to the first gripping sheet and optionally the second gripping sheet.

In some embodiments of this aspect of the disclosure the holding strips can be attached to the fibrous absorbent wicks by an adhesive.

In some embodiments of this aspect of the disclosure the extended distal end of each fibrous absorbent strip is configured to absorb about 20 µl of a liquid.

In some embodiments of this aspect of the disclosure the biological fluid sample collector can further comprise a foldable cover extending from the first gripping sheet and wherein the distal end of the foldable cover is removably secured to the second gripping sheet, thereby enclosing the plurality of fibrous absorbent strips of the sample collecting comb.

In some embodiments of this aspect of the disclosure the distal end of the foldable cover has a tab configured to be removably receivable by a tab receiving slot in the second gripping sheet.

In some embodiments of this aspect of the disclosure the comb of the biological fluid sample collector comprises five fibrous absorbent strips, wherein the sample collecting comb is configured to absorb about 100 µl of a liquid.

In some embodiments of this aspect of the disclosure the fibrous absorbent strips are comprised of absorbent paper, glass fibers, a fibrous polymer, or any combination thereof.

Still another aspect of the disclosure encompasses a kit comprising packaging containing a biological fluid sample collector according to the disclosure, a means to obtain a biological fluid from a human or animal subject, and instructions for obtaining a biological fluid from a human or animal subject and collecting a sample therefrom using the biological fluid sample collector.

In some embodiments of this aspect of the disclosure the biological fluid is blood.

In some embodiments of this aspect of the disclosure the means to obtain a biological fluid is a lancet.

Yet another aspect of the disclosure encompasses embodiments of a method of obtaining a biological fluid sample from a subject animal or human comprising the steps of: (a) contacting a biological fluid from a subject animal or human with a sample collecting comb consisting of a plurality of fibrous absorbent strips, wherein each fibrous absorbent strip has a proximal end disposed between and adhering to a first holding strip and a second holding strip and a distal end extending from the holding strips, and wherein the plurality of fibrous absorbent strips is disposed between a first gripping sheet and a second gripping sheet and wherein the plurality of fibrous absorbent strips are attached to the first gripping sheet and optionally the second gripping sheet; and (b) incubating the plurality of fibrous absorbent strips having the biological fluid sample absorbed thereon with an elution buffer, thereby eluting the biological fluid sample from the fibrous absorbent strips.

In some embodiments of this aspect of the disclosure the extending distal end of each fibrous absorbent strip can absorb about 20 μl of a liquid.

In some embodiments of this aspect of the disclosure the comb of the biological fluid sample collector consists of five fibrous absorbent strips and step (a) comprises collecting about 100 μl of the biological fluid.

In some embodiments of this aspect of the disclosure the method can further comprise the step of obtaining a biological fluid from the subject animal or human. In some embodiments of this aspect of the disclosure the biological fluid is blood.

In some embodiments of this aspect of the disclosure the method can further comprise the step of drying the biological fluid samples absorbed on the five fibrous absorbent strips.

In some embodiments of this aspect of the disclosure the elution buffer can comprise phosphate buffer saline, a protease inhibitor, and a detergent.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Elution Buffer Preparation:

Elution Buffer contains PBS, protease inhibitor (1 vial/6 ml PBS), and 0.1% tween 20. PBS and tween20 can be stored at room temperature. Protease inhibitor should be kept frozen until reconstitution immediately before use. Elution buffer can be kept at room temperature while in use. Unused elution buffer should be aliquoted and stored at −20° C. or colder. Allow buffer to come to room temperature before use.

Example 2

Dried Blood Sample (DBS) Elution:

Cut the Whatman® filter paper strip with clean scissors at the designated line and place into a 1.5 mL conical tube using forceps cleaned with alcohol. Repeat with each Whatman® strip for a particular patient. Elution is with a 1:10 ratio of elution buffer (for example. a 5×10 mm strip should be eluted with 250 μl buffer). Elute for 4 h at room temperature with shaking, vortexed for 10 sec every 30 mins.

After elution, liquid is transferred to a clean 1.5 mL conical leaving the Whatman® strip behind. The liquid is centrifuged at 14,000 rpm for 10 mins and the supernatant collected into a clean 1.5 mL conical tube.

Example 3

Storage of DBS samples: Following elution, the eluted samples should be stored at 4° C. for no more than one day. Any unused eluted samples should be aliquoted, labeled, and stored at −80° C. If storage of original dried blood is required, it should be sealed in a bag with desiccant and stored between about −20° C. and about −80° C.

Dried Blood Sample Stability Test

Test temperature: −80° C.; 4° C.; Ambient; 40° C.; 50° C.; 60° C.

Time points: Day 0; 1 week; 1 month; 2 months; 3 months

Blood elution: 1:10 with buffer

Detection Method: QAH-SAP-1, 20× dilution; Total tips needed: 25 (1+4×6).

The stabilities of a panel of serum proteins (cytokines) at various storage temperatures and periods are presented in Tables 1-3.

TABLE 1

| | −80° C. | | | | 4° C. | | | |
|---|---|---|---|---|---|---|---|---|
| | Week 1 | Month 1 | Month 2 | Month 3 | Week 1 | Month 1 | Month 2 | Month 3 |
| Angiotensinogen | 100% | 100% | 100% | 100% | 100% | 100% | 100% | 100% |
| CHI3L1 | 100% | 100% | 100% | 100% | 100% | 100% | 100% | 100% |
| Cystatin C | 100% | 100% | 100% | 100% | 100% | 100% | 100% | 100% |
| Decorin | 100% | 100% | 100% | 100% | 100% | 100% | 100% | 100% |
| Dkk-3 | 100% | 100% | 100% | 100% | 100% | 100% | 100% | 100% |
| ICAM-1 | 100% | 100% | 100% | 70% | 100% | 100% | 100% | 60% |
| IL-6R | 100% | 100% | 100% | 100% | 100% | 100% | 100% | 100% |
| LAP(TGFb1) | 100% | 100% | 100% | 100% | 100% | 100% | 100% | 92% |
| MIP-1d | 100% | 100% | 100% | 100% | 100% | 100% | 100% | 100% |
| MSP | 100% | 100% | 100% | 100% | 100% | 100% | 100% | 100% |
| NAP-2 | 100% | 100% | 100% | 100% | 100% | 100% | 100% | 100% |

TABLE 1-continued

|  | −80° C. | | | | 4° C. | | | |
| --- | --- | --- | --- | --- | --- | --- | --- | --- |
|  | Week 1 | Month 1 | Month 2 | Month 3 | Week 1 | Month 1 | Month 2 | Month 3 |
| PARC | 100% | 100% | 100% | 100% | 100% | 100% | 100% | 100% |
| P-Cadherin | 100% | 100% | 100% | 100% | 100% | 100% | 82% | 85% |
| PDGF-AA | 100% | 100% | 100% | 100% | 100% | 100% | 100% | 100% |
| PGRP-s | 100% | 100% | 100% | 100% | 100% | 100% | 100% | 100% |
| RANTES | 100% | 100% | 100% | 100% | 100% | 100% | 100% | 100% |
| SCF R | 100% | 100% | 100% | 100% | 100% | 100% | 100% | 90% |
| Siglec-5 | 100% | 100% | 100% | 92% | 100% | 100% | 100% | 72% |
| TIMP-1 | 100% | 100% | 100% | 100% | 100% | 100% | 100% | 81% |
| TIMP-2 | 100% | 100% | 100% | 65% | 100% | 100% | 100% | 66% |
| Average | 100% | 100% | 100% | 96% | 100% | 100% | 99% | 92% |

TABLE 2

|  | Ambient | | | | 37° C. | | | |
| --- | --- | --- | --- | --- | --- | --- | --- | --- |
|  | Week 1 | Month 1 | Month 2 | Month 3 | Week 1 | Month 1 | Month 2 | Month 3 |
| Angiotensinogen | 100% | 100% | 100% | 100% | 100% | 100% | 100% | 100% |
| CHI3L1 | 100% | 100% | 100% | 61% | 100% | 100% | 100% | 29% |
| Cystatin C | 100% | 100% | 100% | 100% | 100% | 100% | 100% | 66% |
| Decorin | 100% | 100% | 100% | 100% | 100% | 100% | 100% | 9% |
| Dkk-3 | 100% | 100% | 100% | 100% | 100% | 93% | 80% | 73% |
| ICAM-1 | 100% | 100% | 100% | 67% | 100% | 100% | 97% | 28% |
| IL-6R | 100% | 100% | 100% | 100% | 100% | 100% | 100% | 48% |
| LAP(TGFb1) | 100% | 100% | 84% | 44% | 100% | 90% | 71% | 30% |
| MIP-1d | 100% | 100% | 100% | 83% | 100% | 100% | 82% | 0% |
| MSP | 100% | 100% | 100% | 100% | 100% | 100% | 100% | 47% |
| NAP-2 | 100% | 100% | 100% | 100% | 100% | 100% | 100% | 97% |
| PARC | 100% | 100% | 100% | 90% | 100% | 100% | 100% | 62% |
| P-Cadherin | 100% | 100% | 83% | 63% | 100% | 98% | 81% | 26% |
| PDGF-AA | 100% | 100% | 100% | 71% | 100% | 100% | 100% | 0% |
| PGRP-s | 100% | 100% | 100% | 100% | 100% | 100% | 90% | 63% |
| RANTES | 100% | 100% | 100% | 100% | 100% | 100% | 100% | 100% |
| SCF R | 100% | 100% | 100% | 90% | 100% | 100% | 100% | 78% |
| Siglec-5 | 100% | 100% | 97% | 83% | 100% | 100% | 95% | 66% |
| TIMP-1 | 100% | 100% | 100% | 81% | 100% | 100% | 100% | 71% |
| TIMP-2 | 100% | 100% | 90% | 63% | 100% | 85% | 84% | 30% |
| Average | 100% | 100% | 98% | 85% | 100% | 98% | 94% | 51% |

TABLE 3

|  | 50° C. | | | | 60° C. | | | |
| --- | --- | --- | --- | --- | --- | --- | --- | --- |
|  | Week 1 | Month 1 | Month 2 | Month 3 | Week 1 | Month 1 | Month 2 | Month 3 |
| Angiotensinogen | 100% | 100% | 100% | 100% | 100% | 100% | 100% | 100% |
| CHI3L1 | 100% | 63% | 27% | 1% | 96% | 13% | 11% | 3% |
| Cystatin C | 100% | 100% | 100% | 0% | 100% | 100% | 12% | 0% |
| Decorin | 100% | 100% | 100% | 0% | 100% | 61% | 100% | 0% |
| Dkk-3 | 100% | 90% | 49% | 2% | 100% | 95% | 61% | 0% |
| ICAM-1 | 100% | 100% | 40% | 4% | 100% | 100% | 44% | 0% |
| IL-6R | 100% | 23% | 21% | 0% | 77% | 11% | 11% | 0% |
| LAP(TGFb1) | 100% | 100% | 56% | 23% | 100% | 74% | 31% | 9% |
| MIP-1d | 100% | 100% | 0% | 0% | 100% | 100% | 1% | 0% |
| MSP | 100% | 100% | 100% | 0% | 100% | 81% | 0% | 0% |
| NAP-2 | 100% | 100% | 100% | 100% | 100% | 100% | 100% | 99% |
| PARC | 100% | 100% | 100% | 43% | 100% | 100% | 100% | 40% |
| P-Cadherin | 100% | 100% | 100% | 11% | 100% | 100% | 100% | 0% |
| PDGF-AA | 100% | 100% | 100% | 0% | 100% | 100% | 0% | 0% |
| PGRP-s | 100% | 86% | 44% | 30% | 88% | 79% | 21% | 19% |
| RANTES | 100% | 100% | 100% | 27% | 100% | 100% | 31% | 18% |
| SCF R | 100% | 100% | 95% | 4% | 100% | 100% | 0% | 0% |
| Siglec-5 | 100% | 100% | 58% | 28% | 100% | 100% | 36% | 18% |
| TIMP-1 | 100% | 100% | 38% | 20% | 100% | 100% | 9% | 4% |
| TIMP-2 | 100% | 56% | 32% | 1% | 74% | 24% | 8% | 0% |
| Average | 100% | 91% | 68% | 20% | 97% | 82% | 39% | 16% |

Accordingly, dried blood serum is stable in ambient temperature for up to 2 months without significant degradation. For long period storage, −80° C. is recommended. One strip of 5×10 cm of WHATMAN CF12® paper takes about 20 µl blood. 100 µl from five strips may be required.

I claim:

1. A method of determining the identities and the expression levels of serum protein biomarkers of a human or animal subject, the method comprising the steps of:
    (a) contacting blood from a subject animal or human with a fluid sample collecting comb, said comb consisting of a plurality of fibrous absorbent strips, wherein each fibrous absorbent strip consists of a fibrous absorbent wick having a proximal end disposed between and adhering to a first holding strip and a second holding strip and a distal end extending from the holding strips, and wherein the plurality of fibrous absorbent strips is disposed between a first gripping sheet and a second gripping sheet and wherein the plurality of fibrous absorbent strips are attached to the first gripping sheet and optionally the second gripping sheet;
    (b) allowing the blood samples absorbed by the fibrous absorbent wicks to dry;
    (c) eluting serum proteins from the blood samples by incubating the fibrous absorbent wicks with an elution buffer;
    (d) determining the identities and levels of the extracted proteins of the subject sample by microarray analysis;
    (e) comparing by computer the identities and levels of the extracted proteins of the subject sample with a reference database generated from the blood samples of a plurality of subjects;
    (f) producing a computer-generated report of the identities and levels of the serum protein biomarkers of the subject, comparing the reported levels of the serum protein biomarkers with the average levels of the same protein biomarkers of the reference database and identifying if the subject has elevated or reduced level of at least one biomarker compared to the level of the biomarker in the database;
    (g) producing a computer-generated report associating an elevated or reduced level of at least one biomarker of the subject with a pathological condition in need of a treatment; and
    (h) adjusting the treatment based on the identities and amounts of the protein biomarkers of the blood sample of the subject.

2. The method of claim 1, wherein the microarray analysis is performed using a low density microarray, an expression microarray, a proteomic array, or an antibody array.

3. The method of claim 1, wherein the microarray analysis comprises identifying a statistical significance level for whether a gene is upregulated or downregulated relative to a reference.

4. The method of claim 3, wherein the statistical significance is determined at a p-value of less than or equal to 0.05.

5. The method of claim 4, wherein the p-value is corrected for multiple comparisons.

6. The method of claim 1, wherein a prioritized list of candidate treatments are identified.

7. The method of claim 6, wherein prioritizing comprises ordering the treatments from higher priority to lower priority according to usable analysis results for serum protein products using microarray analysis.

8. The method of claim 1, further comprising administration of the one or more candidate treatment to the subject.

9. The method of claim 1, wherein the report lists the one or more identified candidate treatments and the biomarker-drug association rules used to identify the one or more identified candidate treatment.

10. The method of claim 1, wherein the report comprises a summary listing of the microarray analysis.

11. The method of claim 1, wherein the report is displayed using a computer display or a printed report.

12. The method of claim 1, wherein the distal end of each fibrous absorbent wick is configured to absorb about 20 µl of a liquid.

13. The method of claim 1, wherein the biological fluid sample collector comprises a sample collecting comb consisting of five absorbent strips, wherein each absorbent strip consists of a fibrous absorbent wick having a proximal end disposed between and adhering to a first holding strip and a second holding strip and a distal end extending from the holding strips, wherein the extending distal end of each fibrous absorbent strip is configured to absorb about 20 µl of a liquid and wherein the plurality of fibrous absorbent strips is disposed between a first gripping sheet and a second gripping sheet and wherein the plurality of fibrous absorbent strips are attached to the first gripping sheet and optionally the second gripping sheet, and further comprising a foldable cover extending from the first gripping sheet, the distal end of the foldable cover having a tab configured to be removably receivable by a slot in the second gripping sheet and wherein the distal end of the foldable cover is removably secured to the second gripping sheet, thereby enclosing the plurality of fibrous absorbent strips of the sample collecting comb.

* * * * *